United States Patent
Maginness et al.

(10) Patent No.: US 8,927,022 B2
(45) Date of Patent: Jan. 6, 2015

(54) GRANULES OF POROUS BIOCOMPATIBLE MATERIALS

(75) Inventors: Max Maginness, Seattle, WA (US); Andrew Marshall, Seattle, WA (US); Christine L. Glaister, Seattle, WA (US); Michel Alvarez, Seattle, WA (US)

(73) Assignee: Healionics Corporation, Seattle, WA (US)

( * ) Notice: Subject to any disclaimer, the term of this patent is extended or adjusted under 35 U.S.C. 154(b) by 0 days.

(21) Appl. No.: 13/511,971

(22) PCT Filed: Mar. 3, 2010

(86) PCT No.: PCT/US2010/026107
§ 371 (c)(1),
(2), (4) Date: Oct. 2, 2012

(87) PCT Pub. No.: WO2011/065987
PCT Pub. Date: Jun. 3, 2011

(65) Prior Publication Data
US 2013/0022648 A1    Jan. 24, 2013

Related U.S. Application Data

(60) Provisional application No. 61/264,585, filed on Nov. 25, 2009.

(51) Int. Cl.
| | |
|---|---|
| *A61K 9/14* | (2006.01) |
| *C08B 37/00* | (2006.01) |
| *B02C 23/08* | (2006.01) |
| *C08F 20/28* | (2006.01) |
| *C08J 9/26* | (2006.01) |
| *A61K 38/18* | (2006.01) |
| *C08G 77/04* | (2006.01) |
| *A61L 27/52* | (2006.01) |
| *A61L 27/56* | (2006.01) |
| *A61L 27/54* | (2006.01) |
| *A61L 27/58* | (2006.01) |

(52) U.S. Cl.
CPC ............... *A61L 27/58* (2013.01); *A61L 27/52* (2013.01); *A61L 2300/406* (2013.01); *A61L 2400/10* (2013.01); *A61L 2300/414* (2013.01); *A61L 27/56* (2013.01); *A61L 27/54* (2013.01); *A61L 2400/06* (2013.01)
USPC .............. 424/489; 525/308; 514/7.6; 521/154

(58) Field of Classification Search
None
See application file for complete search history.

(56) References Cited

U.S. PATENT DOCUMENTS

| | | | |
|---|---|---|---|
| 2,842,775 A | 7/1958 | Pangman | 3/36 |
| 3,293,663 A | 12/1966 | Cronin | 3/36 |

(Continued)

FOREIGN PATENT DOCUMENTS

| | | |
|---|---|---|
| WO | WO 03/093196 A1 | 11/2003 |
| WO | WO 03093196 A1 * | 11/2003 |

(Continued)

OTHER PUBLICATIONS

Barnsley et al., "Textured Surface Breast Implants in the Prevention of Capsular Contracture among Breast Augmentation Patients: A Meta-Analysis of Randomized Controlled Trials," *Plast. Reconstr. Surg. 117*: 2182-2190, Jun. 2006.

(Continued)

*Primary Examiner* — Rachael E Bredefeld
*Assistant Examiner* — Dominic Lazaro
(74) *Attorney, Agent, or Firm* — Seed IP Law Group PLLC

(57) ABSTRACT

The disclosure provides granular forms of porous biomaterials and methods for forming and applying these biomaterials, including uses to promote vascularization and tissue ingrowth.

16 Claims, 5 Drawing Sheets

(56) References Cited

U.S. PATENT DOCUMENTS

| | | | |
|---|---|---|---|
| 3,852,832 A | 12/1974 | McGhan et al. | 3/36 |
| 3,929,971 A | 12/1975 | Roy | 423/308 |
| 3,938,528 A | 2/1976 | Bucalo | 128/334 C |
| 4,073,713 A | 2/1978 | Newman | 204/195 B |
| 4,223,070 A | 9/1980 | Hahn et al. | 428/407 |
| 4,264,990 A | 5/1981 | Hamas | 3/36 |
| 4,388,166 A | 6/1983 | Suzuki et al. | 204/403 |
| 4,400,833 A | 8/1983 | Kurland | 3/1 |
| 4,484,987 A | 11/1984 | Gough | 204/1 T |
| 4,673,409 A | 6/1987 | Van Kampen | 623/23 |
| 4,757,022 A | 7/1988 | Shults et al. | 435/291 |
| 4,820,303 A | 4/1989 | Brauman | 623/8 |
| 4,832,997 A | 5/1989 | Balanzat et al. | 428/131 |
| 4,902,294 A | 2/1990 | Gosserez | 623/8 |
| 4,960,425 A | 10/1990 | Yan et al. | 623/8 |
| 5,002,572 A | 3/1991 | Picha | 623/11 |
| 5,007,929 A | 4/1991 | Quaid | 623/8 |
| 5,022,942 A | 6/1991 | Yan et al. | 156/219 |
| 5,055,307 A | 10/1991 | Tsuru et al. | 424/493 |
| 5,116,650 A * | 5/1992 | Bowser | 428/34.2 |
| 5,518,680 A | 5/1996 | Cima et al. | 264/401 |
| 5,589,176 A | 12/1996 | Seare, Jr. | 424/400 |
| 5,605,693 A | 2/1997 | Seare, Jr. | 424/400 |
| 5,624,674 A | 4/1997 | Seare, Jr. | 424/400 |
| 5,681,572 A | 10/1997 | Seare, Jr. | 424/400 |
| 5,753,014 A | 5/1998 | Van Rijn | 96/12 |
| 5,964,803 A | 10/1999 | Iversen et al. | 623/8 |
| 6,030,635 A * | 2/2000 | Gertzman et al. | 424/423 |
| 6,520,997 B1 | 2/2003 | Pekkarinen et al. | 623/23.72 |
| 6,702,857 B2 | 3/2004 | Brauker et al. | 623/23.76 |
| 6,857,932 B2 | 2/2005 | Chen | 450/38 |
| 6,875,386 B1 | 4/2005 | Ward et al. | 264/154 |
| 7,361,158 B1 | 4/2008 | Mooney, Jr. | 604/174 |
| 7,364,592 B2 | 4/2008 | Carr-Brendel et al. | 623/23.76 |
| 7,972,628 B2 | 7/2011 | Ratner et al. | 424/499 |
| 2003/0074081 A1 | 4/2003 | Ayers | 623/23.5 |
| 2003/0180376 A1* | 9/2003 | Dalal et al. | 424/602 |
| 2004/0086548 A1 | 5/2004 | St. John et al. | 424/445 |
| 2005/0031689 A1 | 2/2005 | Shults et al. | 424/473 |
| 2005/0228477 A1 | 10/2005 | Grainger et al. | 623/1.11 |
| 2006/0136071 A1* | 6/2006 | Maspero et al. | 623/23.76 |
| 2006/0276831 A1 | 12/2006 | Porter et al. | 606/200 |
| 2007/0087031 A1* | 4/2007 | Ashman et al. | 424/423 |
| 2008/0075752 A1 | 3/2008 | Ratner et al. | 424/426 |
| 2008/0200430 A1 | 8/2008 | Bitterman et al. | 514/55 |
| 2009/0012625 A1 | 1/2009 | Ying et al. | 623/23.63 |
| 2009/0048537 A1 | 2/2009 | Lydon et al. | 600/585 |
| 2009/0254194 A1 | 10/2009 | Peters et al. | 623/23.61 |
| 2011/0287078 A1 | 11/2011 | Ratner et al. | 424/422 |

FOREIGN PATENT DOCUMENTS

| | | | |
|---|---|---|---|
| WO | WO 2005/032418 A2 | | 4/2005 |
| WO | WO 2005032418 A2 * | | 4/2005 |
| WO | WO 2009/077210 A1 | | 6/2009 |
| WO | WO 2011/065987 A1 | | 6/2011 |

OTHER PUBLICATIONS

Brauker et al., "Neovascularization of synthetic membranes directed by membrane microarchitecture," *J Biomed Mater Res* 29: 1517-1524, 1995.

Madden et al., "Proangiogenic scaffolds as functional templates for cardiac tissue engineering," *Proc. Nat. Acad. Sci. 107*(34): 15211 (6 pages), 2010.

Marshall et al., "Biomaterials with Tightly Controlled Pore Size that Promote Vascular In-Growth," *Polymer Preprints* 45(2): 100-101, 2004.

Paul et al., "Topographical control of human macrophages by a regularly microstructured polyvinylidene fluoride surface," *Biomaterials* 29: 4056-4064, 2008.

Rosengren et al., "Pore size in implanted polypropylene filters is critical for tissue organization," *J Biomed Mater Res* 67A: 918-926, 2003.

Sharkawy et al., "Engineering the tissue which encapsulates subcutaneous implants. II. Plasma-tissue exchange properties," *J Biomed Mater Res* 40: 586-597, 1998.

Tsai, "Engineering biomaterial interfaces to control foreign body response: reducing giant cell formation and understanding host response to porous materials," Ph.D. Dissertation, University of Washington, 2007 (151 pages).

* cited by examiner

GRANULES OF POROUS BIOCOMPATIBLE MATERIALS

CROSS-REFERENCE TO RELATED APPLICATION

This application claims the benefit under 35 U.S.C. §119 (e) of U.S. Provisional Patent Application No. 61/264,585 filed Nov. 25, 2009, where this provisional application is incorporated herein by reference in its entirety.

TECHNICAL FIELD

This invention relates generally to biocompatible materials and more particularly to scaffold structures that support tissue growth and promote healing.

BACKGROUND

An implanted biomaterial with well-controlled architecture can elicit beneficial biological responses. In particular, biomaterials with interconnecting pores are known to promote neovascularization and angiogenesis within the pores. For instance, porous biomaterials with pore size large enough to allow macrophage penetration result in increased vascularity in the capsule tissue. Brauker J. H. et al., *J Biomed Mater Res* 29, 1517 (1995). Increased vascularity was also shown to correlate with improved diffusion and plasma-exchange properties. Sharkaway A. A. et al., *J Biomed Mater Res* 40, 586 (1998). Certain pore sizes were recognized as allowing an increased colonization of host macrophages within the pore structure and maximizing the density of new vessels within the porous material. These proangiogenic characteristics of the porous biomaterials make them particularly useful as scaffolds for stimulating tissue growth and promoting wound healing.

Known porous biomaterials typically allow tissue ingrowth in an implant to a depth of approximately 0.2 mm to about 1 mm from the surface of the implant. This limitation of the extent of vascularization is due, at least in part, to mechanical constraints on the size of blood vessels that can develop via angiogenesis in and through the interconnected porous structure. Thus, there is a need for developing biomaterials that allow extensive tissue ingrowth.

SUMMARY

A granular porous biomaterial with pre-selected granule size and pre-determined pore sizes is described. In certain embodiments, the granular porous biomaterial is a suitable scaffold for supporting extended tissue ingrowth.

More specifically, in certain embodiments, a composition is provided comprising granules that are made of a porous biocompatible material having a plurality of substantially connected pores, wherein the diameter of pores within the granules generally ranges from about 5 µm to about 100 µm and wherein the volume of an individual granule is at least the volume of a sphere of at least about 0.1 mm diameter equivalent and not more than the volume of a sphere of about 2 mm diameter equivalent. In this size range, each granule contains from about 30 to about 30,000 interconnected pores.

In various embodiments, substantially all the pores may have a similar diameter, the mean of which is between about 5 and about 100 micrometers. Furthermore, substantially all the pores are each connected to at least two other pores by respective interconnecting passages, and often to at least four other pores. In various embodiments, each granule has an internal porosity, which is the collective volume of the pores measured against the volume of the granule, from about 60% to about 75%.

Granules may be dispensed into normal tissue or wound sites by a syringe, with or without a needle, or by some other similar purpose device. The granule material or the granule surface area or both may be used as a reservoir and delivery means for biologically active substances, such as antibiotics, drugs (including anti-fibrotic drugs) or growth factors.

Granules are prepared from a larger piece of substantially connected porous biomaterial. Generally, the larger piece of material is ground to form granules. The biomaterial can be degradable. In various embodiments, the biomaterial comprises medical-grade silicone or hydrogel.

One embodiment provides a composition comprising one or more granules made of a porous biocompatible material having a plurality of substantially connected pores, wherein pores within the granules range from about 5 µm to about 100 µm in diameter and wherein each granule has a volume that is at least the volume of a sphere of at least about 0.1 mm diameter equivalent and not more than the volume of a sphere of about 2 mm diameter equivalent.

In another embodiment, the volume of an individual granule is not more than the volume of a sphere of about 1 mm diameter equivalent. In another embodiment, the volume of an individual granule is at least the volume of a sphere of about 100 µm and not more than the volume of a sphere of about 400 µm diameter equivalent. In another embodiment, each granule has an internal porosity of about 60% to about 75%. In another embodiment, each granule has an aspect ratio of not more than 5. In another embodiment, the pores within each granule have a mean diameter of between about 20 µm and 40 µm. In another embodiment, two connecting pores within a granule define a throat diameter that is about 15% to 40% of the diameter of each of the two connecting pores.

In various other embodiments, the composition may further comprise a biocompatible fluid, wherein the granules are suspended in the biocompatible fluid. In another embodiment, the biocompatible fluid is bio-resorbable. In another embodiment, the biocompatible fluid comprises sodium hyaluronate or saline. In another embodiment, the composition is injectable. In various other embodiments, the biocompatible liquid is bioactive or comprises a bioactive ingredient. In another embodiment, the bioactive ingredient is an antibiotic, a drug, or a growth factor. In another embodiment, the granules are formed of medical-grade silicone or a hydrogel. In another embodiment, the hydrogel is poly(2-hydroxyethyl methacrylate). In another embodiment, the granules are formed of a biodegradable material. In another embodiment, the biodegradable material is capable of degrading in the presence of a chemical or enzyme. In another embodiment, the biodegradable material comprises cross-linked hyaluronic acid and the enzyme is hyaluronidase. In various other embodiments, the granules further comprise a drug or a sensor of a body condition.

Another embodiment provides a method, which comprises introducing a composition to a part of an animal or human in an effective amount to effect tissue growth, wherein the composition comprises one or more granules made of a porous biocompatible material having a plurality of substantially connected pores, wherein pores within the granules range from about 5 µm to about 100 µm in diameter and wherein each granule has a volume that is at least the volume of a sphere of at least about 0.1 mm diameter and not more than the volume of a sphere of about 2 mm diameter, and wherein the tissue growth comprises tissue growth that takes place within the plurality of pores.

In another embodiment, the composition further comprises a biocompatible fluid and is injectable. In another embodiment, the granules are injected into a wound site. In another embodiment, the granules are introduced into tissue, soft tissue or bone. In another embodiment, the granules cause tissue expansion. In another embodiment, two connecting pores within a granule define a throat diameter that is about 15% to 40% of the diameter of each of the two connecting pores. In another embodiment, the granules define interstitial spaces that have a diameter larger than the throat diameter between two connecting pores. In another embodiment, a dimension of the interstitial spaces is about 15% to about 60% of a diameter equivalent of each granule. In another embodiment, each granule has an aspect ratio of not more than 5. In another embodiment, the pores within each granule have a mean diameter of between about 20 and 40 µm.

Yet another embodiment provides a biocompatible scaffold, which comprises one or more granules made of a porous biocompatible material having a plurality of substantially connected pores, wherein pores within the granules range from about 5 µm to about 100 µm in diameter and wherein each granule has a volume that is at least the volume of a sphere of at least about 0.1 mm and not more than the volume of a sphere of about 2 mm diameter equivalent, and wherein the granules are arranged such that they define interstitial spaces, a dimension of the interstitial spaces being about 15% to about 60% of a diameter equivalent of each granule. In another embodiment, the pores within each granule have a mean diameter of between about 20 and 40 µm. In various other embodiments, two connecting pores within a granule define a throat diameter that is about 15% to 40% of the diameter of each of the two connecting pores. In another embodiment, the interstitial spaces have a diameter larger than the throat diameter between two connecting pores.

In another embodiment there is provided a method for making granules of substantially connected porous biocompatible material, the method comprising: forming a slab of a biocompatible material surrounding an array of monodisperse porogens, wherein the porogens have a mean diameter of between about 5 to 100 µm; grinding the slab of the biocompatible material into granules, each granule including two or more porogens; and removing the porogens. In another embodiment, the porogens in the array of monodisperse porogens are fused by sintering prior to the step of slab formation. In another embodiment, each granule has a diameter equivalent of at least about 0.1 mm and not more than about 2 mm. In another embodiment, the method further comprises sorting the granules by size. In another embodiment, sorting the granules comprises sifting the granules into one or more specific size ranges. In another embodiment, the specific size ranges are selected from (1) about 0.1 to about 0.2 mm, (2) from about 0.3 mm to about 0.5 mm and (3) from about 0.7 mm to 1.0 mm. In another embodiment, each granule has an aspect ratio of not more than 5. In another embodiment, the pores within each granule have a mean diameter of between about 20 and 40 µm.

These and other aspects of the herein described invention embodiments will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE DRAWINGS

FIG. 4 is the result observed after 7 days showing cell infiltration 1-2 pores deep in each granule. FIG. 5 shows that, 28 days after introduction, ingrowth from the surrounding native tissue extended throughout the volume filled by granules, and larger blood vessels developed between the granules.

DETAILED DESCRIPTION

Porous biocompatible materials can be used as scaffolds to support tissue growth, especially in vivo. Certain embodiments of the invention described herein surprisingly overcome previously recognized limitation of porous biocompatible materials, by supporting tissue ingrowth distances in excess of approximately 0.2 mm to 1 mm from the porous material surface. Thus, in certain exemplary embodiments described herein, granular porous biomaterials are provided that have pre-selected granule sizes and pre-determined pore sizes. The granular porous biomaterial is suitable for use as a scaffold that allows for tissue ingrowth in an extended volume.

One such embodiment provides a composition comprising granules made of a porous biocompatible material, the biocompatible material having a plurality of substantially connected pores, wherein the diameter of pores within the granules generally ranges from about 5 µm to about 100 µm, and wherein the volume of an individual granule is at least the volume of a sphere of at least about 0.1 mm diameter and not more than the volume of a sphere of about 2 mm diameter. In this size range, each granule may contain from about 30 to about 30,000 interconnected pores.

The shapes and sizes of the granules are selected or controlled such that the granules may be packed into a granular scaffold with interstitial voids or spaces among the granules, the width of the majority of which spaces is larger than or at least equal to the size of the passages between any two interconnecting pores within a granule. The interstitial spaces thus allow for development of larger blood vessels than those that can form inside the individual granules.

Figure 1:
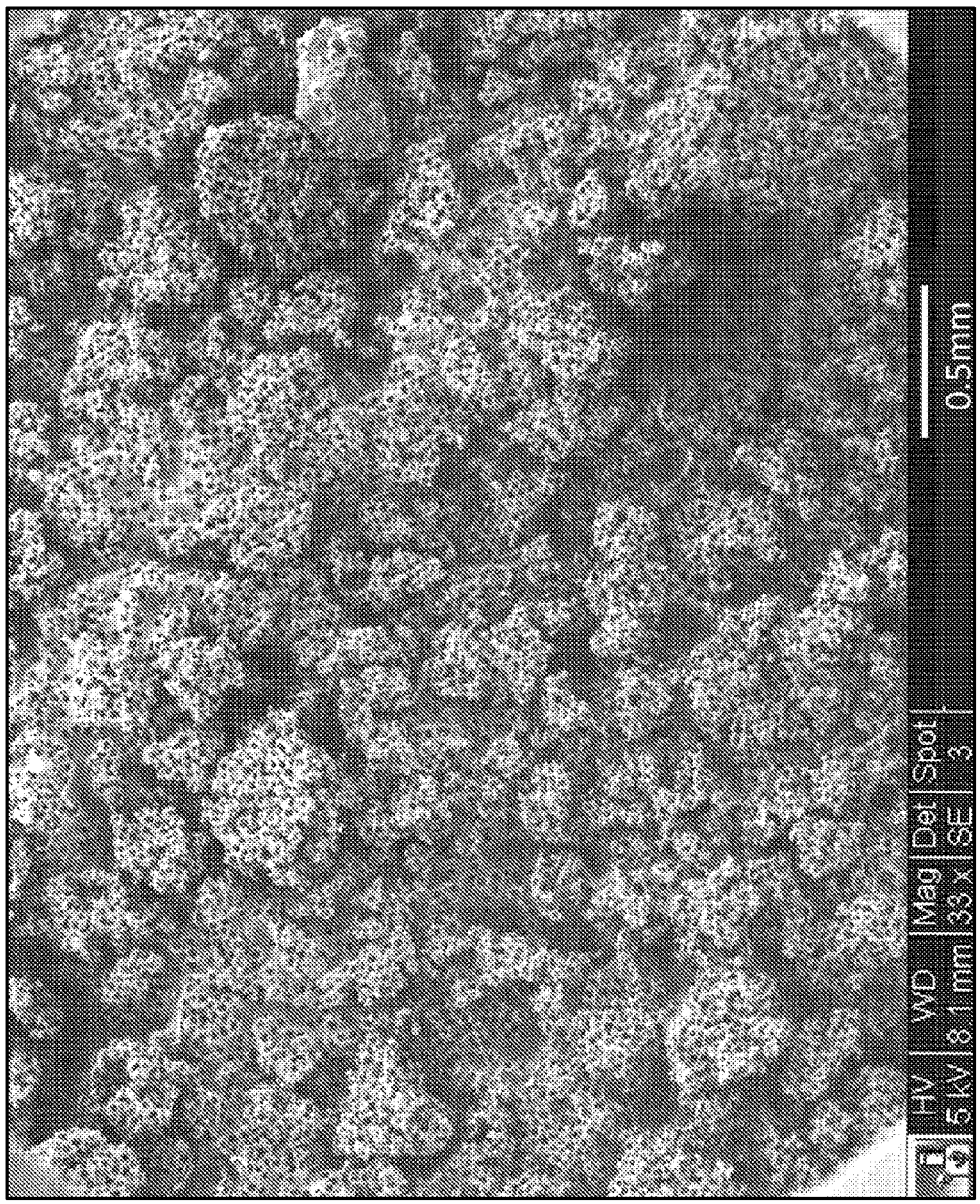
FIG. 1 is a scanning electron microscope (SEM) image of granules made of substantially connected porous biomaterial
Figure 2:
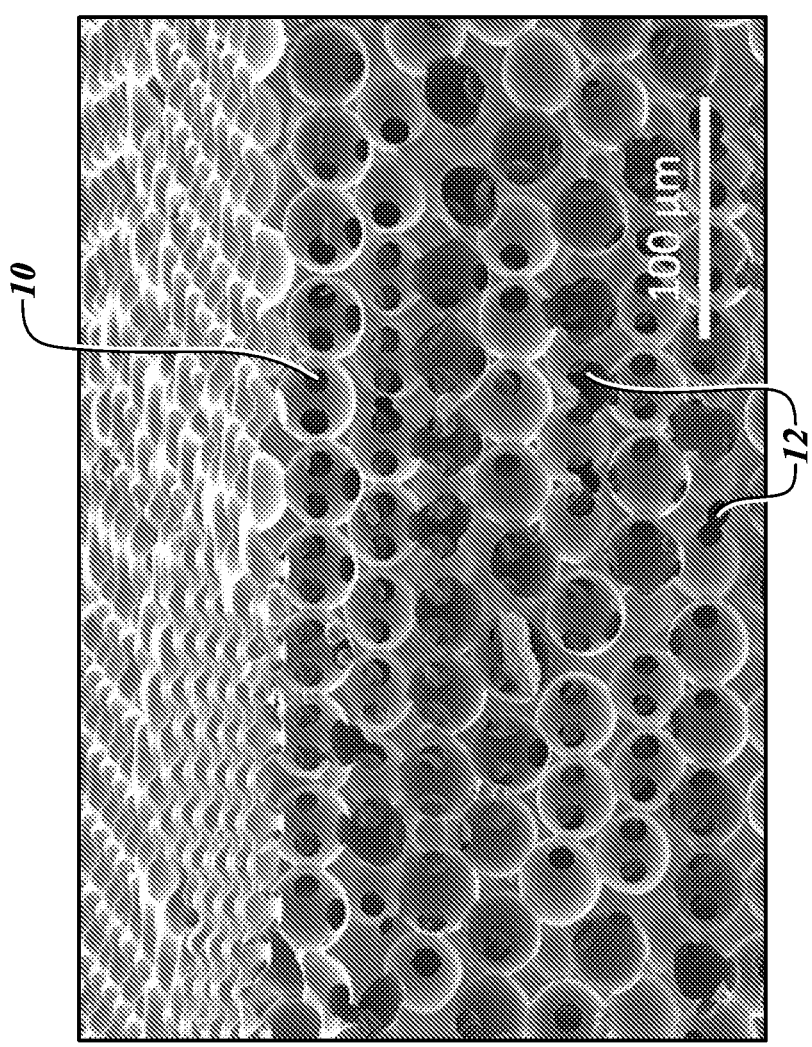
FIG. 2 is an enlarged SEM image of substantially-connected porous biomaterial.

FIG. 1 is an SEM image of an exemplary arrangement of the presently described granules with interstitial spaces between granules. The granules are formed of a biocompatible material; an enlarged image of the pores 10 is shown in FIG. 2.

It is believed according to non-limiting theory that following introduction of the herein described porous granules in vivo, angiogenesis within the pores triggers the growth of larger blood vessels between the granules. The larger blood vessels in turn supply nutrients to further stimulate angiogenesis within the pores, resulting in an augmented vascularization process and a significantly greater degree of tissue ingrowth than would have been possible in a similarly situated non-granular porous material, or a granular non-porous material. In particular, the augmented (e.g., increased in a statistically significant manner relative to an appropriate control) vascularization may, for example, ensure that no part of a porous granule is at a distance greater than about 0.1 mm to about 1 mm from a substantial blood supply. The herein described granules having pore dimensions and volumetric dimensions as presently disclosed thus overcome previously observed distance limits on angiogenesis that were imposed by size and geometry of the pores and interconnecting passages. The present embodiments are therefore capable of promoting viable tissue ingrowth throughout the entire volume occupied by the granules. The more sustained and extensive tissue integration afforded by the instant porous granules having defined geometry, i.e., specified granule volumes and specified pore sizes (e.g., pore diameter) also collaterally reduces the development of fibrotic encapsulation around the biomaterial relative to that seen using biomaterials that lack these geometric features.

Granules may be used in either a wet or dry form. Wet forms typically comprise a slurry, suspension, dispersion, or the like, of granules in a biocompatible liquid, typically, for example, an aqueous liquid that is viscous, such as a dilute solution of hyaluronic acid or other biocompatible compound, such as proteoglycans, glycosaminoglycans (GAGS), heparan sulfate, natural or synthetic polymers, or thixotropic agents. For in vivo administration, granules can be applied in a variety of ways, including by injection into an internal body site, introduction as a filler into a wound or other body cavity site, or placement into a cell culture well to simulate an in vivo tissue environment in vitro. Examples of body cavities include wounds, abscesses, abdominal cavity, chest (thoracic) cavity, intracranial cavity, and others. Granules, or suspensions containing granules, or both may also include other compounds, such as one or more drugs, growth factors or antibiotics, as may desirably be included depending on the particular condition.

Porous Biocompatible Material

Implementations of porous biocompatible materials have been shown to allow ingrowth of tissue, and especially of blood vessels (U.S. Application Publication No. 2008/0075752, the disclosure of which is incorporated in its entirety). The structure of such porous biocompatible materials comprises an array of often spherical or substantially spherical pores that are substantially connected. According to the incorporated disclosure, "substantially connected" means that essentially every pore is connected to at least four other pores. Each pore has a diameter. An opening caused by two pores partially fused into each other, which is called a throat (visualized as the dark "holes" 12 in FIG. 2) also has a diameter. The diameter of a throat might range from infinitesimally small, when two pores are barely fused, to nearly the diameter of a pore, when two pores are almost completely fused. Pores formed according to the incorporated disclosure provide controlled ranges of pore size and throat sizes, such as from approximately 15% to approximately 40% of the pore diameter in order to optimize the angiogenic and anti-fibrotic properties of the porous materials. Numerous criteria exist for assessing angiogenesis and fibrosis in vivo and in vitro and will be known to persons familiar with the relevant art. E.g., Oates et al. *Biomaterials* 28, 3679 (2007); Rosengren et al. *J Biomed Mater Res* 67A, 918 (2003).

Typically, the mean diameter of the pores may be between about 20 and about 90 microns ($\mu m$), such as between about 25 and 75 $\mu m$ or between about 30-60 $\mu m$. In certain preferred embodiments, the mean diameter of the pores may be between about 30 and 40 $\mu m$.

A variety of materials and methodologies are known for the production of a porous biocompatible material and may be adapted to produce the herein described granules having advantageously defined geometry, i.e., specified granule volumes and pore sizes. Briefly, and by way of non-limiting example, porous biocompatible materials may often be made by (1) sintering or fusing (partially or fully) an array of porogens, comprising the substance that forms the pores, (2) casting a biocompatible material into the spaces among fused porogens and then (3) dissolving away, evaporating or otherwise removing the porogens to yield a network of interconnected voids (pores). The partially fused or sintered porogens form what will be the interconnecting throats of the porous material. It is generally most convenient to prepare sintered porogens in a mold. The size of the mold may be any size that is larger than the intended size of granules. A convenient mold size is about 5 cc to 10 cc in volume, e.g., about 3 cm×2 cm×1 cm.

Although porogens may be any shape, (e.g., spherical, cubic, polyhedrons such as dodecahedrons, ellipsoids, cylindrical, irregular), generally porogens are spherical or nearly spherical in shape. Spherical shapes can be efficiently, tightly packed together while still retaining controlled spaces between the porogens, resulting in a highly interconnected network of pores.

The porogens may vary in size. However, their sizes are generally controlled and at least a majority, and more typically, substantially all of the porogens have a diameter that is at least about 10 $\mu m$ and not more than about 90 $\mu m$. In some circumstances, the range of diameters of porogens is less, e.g., from about 20 $\mu m$ to about 75 $\mu m$, from about 20 $\mu m$ to about 30 $\mu m$, from about 30 $\mu m$ to about 60 $\mu m$, or from about 30 $\mu m$ to about 40 $\mu m$, e.g., about 31, 32, 33, 34, 35, 36, 37, 38, 39, 40, 41, 42, 43, 44, 45, 46, 47, 48, 49 or 50 $\mu m$. Size can be controlled by any number of ways. For example, porogens can be sized by sieving or by the manufacturing method used to generate them. In some circumstances, substantially all the porogens have a similar diameter. As used herein, the term "substantially all the porogens" refers to the percentage of porogens within one standard deviation on either side from the mean diameter, within two standard deviations on either side, or within three standard deviations on either side. The term "diameter of a porogen" refers to the longest line segment that can be drawn that connects two points within the pore, regardless of whether the line passes outside the boundary of the pore. In preferred embodiments, the porogens are monodisperse, i.e., the porogens have substantially the same diameters and the difference in the diameters of any two porogens is no more than 20% of the larger diameter.

Porogens may be manufactured from a variety of materials. Generally, the material will in certain embodiments be hard and rigid enough to withstand grinding. Many suitable materials are known for such use and may vary depending on the selected biocompatible material in which pore formation is desired, and on the fabrication process that is employed. One such material is polymethylmethacrylate (PMMA). Other examples of suitable hard materials for use as porogens include metals, composites and ceramics. In addition to its hardness, the material needs to be extractable from the biocompatible material forming the scaffold. Chemical extraction using acetone, di-chloromethane or other suitable solvent is typically used, although physical methods that selectively remove porogens (e.g., by application of heat and/or pressure) may also be used. At times, extraction conditions may involve both chemicals and physical parameters (e.g., temperature, elevated pressure, or reduced pressure).

The shape and diameter of a pore typically may reflect the shape and diameter of a given porogen. In certain embodiments, the pores may be slightly smaller or larger (e.g., ±1-10% volume) than the loose porogens before they are arrayed and sintered due, in part, to the potential shrinking or swelling of the biomaterial following the removal of the porogens. The diameter and shape of the pores, as well as the connections between them may be assessed using scanning electron microscopy (see, e.g., FIG. 2).

Generally, in certain embodiments described herein the diameter of throats resulting from packed and fused porogens is between about 15% to about 40% of the mean diameter of the porogens. As used herein, the term "diameter of throats" refers to the diameter of the cross-section of the connection between two pores in the plane normal to the line connecting the centroids of the two pores (if pores had uniform mass), where the plane is chosen so that the area of the cross-section of the connection is at its minimum value.

In addition, packing usually places each porogen in contact with about four to about twelve other porogens. The packed porogen array and the resulting porous biocompatible scaffold which is formed around the porogens can be any thickness and, in certain embodiments described herein, is usually at least 70 μm or most often at least 100 μm.

The biocompatible material is typically a polymer or any of a number of other biocompatible materials known to the art that are capable of being formed into granules having volumetric and pore dimensions as described herein, and also being capable of maintaining such dimensions when exposed to biochemical and physicochemical forces of the physiological milieu following introduction in vivo. A typical polymer thus may comprise any biocompatible polymer, such as synthetic polymers, naturally-occurring polymers, or mixtures thereof. Exemplary synthetic biocompatible polymers include, but are not limited to, 2-hydroxyethyl methacrylate (HEMA), silicone such as Nusil MED-6215 or other silicone suitable for implantation, poly(epsilon-caprolactone) dimethylacrylate, polysulfone, (poly)methyl methacrylate (PMMA), soluble Teflon-AF, poly ethylene teraphthalate (PET, Dacron), Nylon, polyvinyl alcohol, polyurethane, hydroxyapatite, and mixtures thereof. Exemplary naturally-occurring biocompatible polymers include, but are not limited to, fibrous or globular proteins, complex carbohydrates, glycosaminoglycans, connective tissue extracellular matrix (ECM) components, such as collagen or fibrin, or mixtures thereof. Thus, the polymer scaffold may include collagens of all types, elastin, laminin, hyaluronic acid, alginic acid, desmin, versican, matricellular proteins such as SPARC (osteonectin), osteopontin, thrombospondin 1 and 2, fibrin, fibronectin, vitronectin, albumin, etc. Natural polymers may be used as substantial components of the scaffold or as additives to improve the biocompatibility of a scaffold that comprises a synthetic polymer. Other biocompatible materials suitable for forming the porous biomaterial scaffold may include hydroxyapatite and a variety of biocompatible metals including but not restricted to titanium. Further exemplary biocompatible materials can be found in, e.g., U.S. Application Publication Nos. 2009/0012625 and 2008/0200430, which are incorporated herein by reference in their entireties.

Optionally, the biocompatible material may in certain embodiments be degradable or bioresorbable. Degradation may occur via natural processes such as in vivo metabolic pathways, or by hydrolysis or following treatment with, e.g., an enzyme or chemical that acts upon the biocompatible material. For example, the biocompatible material may comprise crosslinked hyaluronic acid and may be degraded by hyaluronidase. Other suitable biodegradable materials include fibrin and collagen. For some applications, it may be desirable to use granules comprising combinations of biodegradable materials that degrade at different rates.

The biocompatible material may in certain embodiments possess bioactivity due to incorporation into the material of a biologically active ingredient, or may be made partially or solely of a bioactive substance, such as salicylic acid, or of a substance that responds to electrical stimulation, such as polyaminoarenes. The biocompatible material may also be composed partially or solely of an electrically conducting polymer, or the surface of the biomaterial may be metalized.

Granules of Porous Biocompatible Material

The granules of a porous biomaterial can be used to fill a void or expand tissue. The granules, depending on their sizes and geometries, may be packed such that the interstitial spaces between granules are of a predetermined average dimension, which allows development of larger blood vessels and a greater volume of tissue growth than can form within the continuously porous biocompatible material. The large blood vessels are believed to supply nutrients to facilitate vascularization and tissue growth that take place within the pores.

Granules of porous biocompatible material may in certain embodiments comprise pieces of a larger material. In one simple implementation, for example, a biocompatible material—before porogens are extracted—may be mechanically broken into smaller pieces by grinding, shattering, shearing, sonicating, or the like, to obtain granules. Granules of a desired size can be selected from the resultant population of granules.

Many different tools and machines are readily available that may be used for making granules, as will be recognized by persons of skill in the art based on the disclosure herein, and as may vary as a function of the particular biocompatible materials and/or porogens that are used. For example, a coffee grinder is a suitable machine. Other devices include blenders, crushers, sonicators, hammers, mills, and pulverizers.

Generally, a porous biocompatible material is manufactured and granules are obtained before the porogens are extracted. With porogens present, the material has increased physical integrity, allowing it to better withstand granulization. The porous biocompatible biomaterial can also be formed into granules after extraction of the porogens. An exemplary suitable method for polymers comprises freezing the material into rigid form before grinding. The granules prepared as described herein are, although generally irregularly-shaped, approximately spherical in shape or have an aspect ratio of no more than 5, or more preferably, no more than 4, or more preferably no more than 3 (see, e.g., FIG. 1). The term "aspect ratio" refers to the ratio of the largest dimension divided by the smallest dimension of a granule.

Granules obtained by any of the described methods may be subsequently sieved to obtain a preparation of granules that are substantially within a specific size range. There are both practical and biological considerations regarding size ranges of granules. Practically, manufacturing a porous granule of a size having a diameter that is only a few times the average diameter of the pores can be difficult. Further and in a biological context, following emplacement in vivo such granules may not present sufficient interstitial spaces to enable angiogenesis of larger blood vessels, and/or they may block continuity of a blood vessel channel between the granules. According to certain contemplated embodiments, granules that are too small, e.g., having less than about 0.1 mm diameter, should be discarded. Conversely, when granules are too large (e.g., more than 2 mm diameter), there may be insufficient tissue ingrowth through the porous biocompatible material and the granules may be difficult to inject or position.

In certain embodiments, the sizes of the granules are expressed in terms of dimensions (e.g., diameters) as determined by passing through a mesh or sieve having specifically sized mesh openings. In particular, granules may be sieved or otherwise sized to yield a size range from about 0.1 mm to about 2 mm, from about 0.1 mm to about 1 mm, from about 0.1 mm to about 0.8 mm, from about 0.1 mm to about 0.6 mm, from about 0.1 mm to about 0.4 mm, from about 0.1 mm to about 0.2 mm, from about 0.2 mm to about 2 mm, from about 0.2 mm to about 1 mm, from about 0.2 mm to about 0.8 mm, from about 0.2 mm to about 0.6 mm, from about 0.2 mm to about 0.4 mm, from about 0.2 mm to about 0.3 mm, from about 0.3 mm to about 2 mm, from about 0.3 mm to about 1 mm, from about 0.3 mm to about 0.8 mm, from about 0.3 mm to about 0.6 mm, from about 0.3 mm to about 0.5 mm, from about 0.4 mm to about 2 mm, from about 0.4 mm to about 1 mm, from about 0.4 mm to about 0.8 mm, from about 0.4 mm to about 0.6 mm, from about 0.5 mm to about 2 mm, from about 0.5 mm to about 1 mm, from about 0.5 mm to about 0.8 mm, from about 0.6 mm to about 2 mm, from about 0.6 mm to about 1 mm, from about 0.8 mm to about 2 mm, from about 0.8 mm to about 1 mm, from about 1 mm to about 2 mm. Granules larger than the desired range may be reground and sieved. For sieving, the dimensions above apply only to the least dimension of the granules.

In other embodiments, the size of a granule can be expressed as the diameter of a sphere that has substantially the same volume. Thus, when a granule is characterized by its "diameter equivalent" it should be understood that the term refers to the diameter of a sphere with substantially the same volume as a granule. "Substantially the same" refers to at least 70, 75, 80, 85, 90, 95, 96, 97, 98 or 99% and not more than 130, 125, 120, 110, 105, 104, 103, 102, 101 or 100% of the volume of the granule.

Following preparation of granules and any size selection, the porogens may be extracted by chemical or physical method appropriate to the composition of the porogen and of the granules (i.e., the biocompatible material). Optionally, granules may then be coated or impregnated with a chemical or biological substance, such as a drug, growth factor, or sensor of body condition. Coating may be accomplished by dipping (or by suspending, bathing, rinsing, spraying, etc., or other method of contacting) granules in the chemical or biological substance, presented either in liquid or dry form. More uniform and quantitative coating can be obtained with the chemical or biological substance in liquid form. Higher amounts of loading can be obtained by first swelling the granules in a solvent. For example, soaking silicone granules in a protein-loaded suspension or solution comprising a solvent such as isopropanol causes the silicone to swell and take up the protein-loaded liquid. The solvent is then evaporated, resulting in granules that have incorporated the protein (or other chemical or biological substance) into the bulk. The choice of a solvent will depend in part on the composition of the biocompatible material and of the substance to be loaded. A solvent that swells the biomaterial substrate and dissolves the substance without deactivating the substance may be desirable in these and related embodiments. Any substance that dissolves in a solvent without deactivating the substance can be incorporated this way. Solvents for the substance that do not swell the biomaterial substrate may also be used to load the substance into the pore surfaces or open volumes without incorporating the substance into the bulk of the substrate. Some suitable solvents include xylene and other benzene derivatives, isopropanol, acetone and other ketones, and chlorohydrocarbons such as dichloromethane.

Chemical substances may, in certain contemplated embodiments, include chemicals that are sensitive to a stimulus, such as ultrasound, electrical impulse, electromagnetic radiation, light, or temperature. These may include chemicals that are sensitive to levels of oxygen or glucose in the body and that are capable, for instance, of displaying glucose-proportional fluorescence when activated by light. Molecules capable of exhibiting glucose-sensitive fluorescence include fluorescein isothiocyanate-labeled dextran, concanavalin A, rhodamine-concanavalin A, glucose oxidase, glucose dehydrogenase, hexokinase/glucokinase, bacterial glucose-binding protein, and boronic acid derivatives. Biological substances may, in certain contemplated embodiments, include growth factors (e.g., fibroblast growth factors, stem cell growth factors, platelet-derived growth factor, transforming growth factor beta, insulin-like growth factors, epidermal growth factor, vascular endothelial growth factor, angiopoietins, interleukins, granulocyte-colony stimulating factor, granulocyte macrophage colony stimulating factor, nerve growth factor, and keratinocyte growth factor), vitamins (e.g., vitamin A, vitamin C, vitamin E), fibrinogen, fibronectin, bone morphogenetic proteins, cytokines such as interleukins, lymphokines, chemokines, tumor necrosis factor-$\alpha$, and interferons, leptins, cell adhesion molecules or portions thereof (e.g., RGD peptides, ICAM, NCAM, VCAM, integrins, CD44), antibacterial compounds or peptides, and enzymes (e.g., collagenase, plasminogen activator, proteases).

Granules may also be surface-modified with substances that are hydrophilic, such as polyethylene glycol or tetraglyme or alumina; and/or that are hydrophobic, such as polytetrafluoroethylene or silicone; and/or that increase lubricity, such as hyaluronic acid; and/or that improve cell adhesion, such as carbonyldiimidazole (with or without coupled proteins such as collagen); and/or that are radiopaque, such as noble metals; and/or that are antimicrobial, such as silver ions or antimicrobial peptides, among others. For example, modifying the surfaces of granules with RGD (arginine-glycine-aspartic acid) peptides may increase cell adhesion to granules.

Granules may also be sterilized in a variety of ways. The granules may be sterilized with ethylene oxide gas, irradiated, autoclaved, or soaked in organic solvents, or sterilized by other ways known to those skilled in the art.

As described herein, an advantage to using the herein described granules as biological scaffolds, for instance, to promote tissue growth and/or repair of sites of granule administration in vivo, is that the interstitial spaces among and between granules may be sized to allow development of larger blood vessels and of a greater degree and/or volume of tissue growth than can form within the continuous porous biocompatible material. To realize this advantage, generally the interstitial spaces among and between granules will, in certain preferred embodiments, have a diameter that is larger than the diameter of intragranular throats between pores, thereby accommodating interstitial ingrowth of larger diameter blood vessels than can form inside the individual porous granules. Typically, when granules are packed in a cavity, the dimension of interstitial spaces will range from about 15% to about 60% of the diameter equivalent of the granules.

Delivery of Granules

Granules may be delivered to tissue sites in animals, including humans, in a variety of ways, including by injection, by direct introduction or implantation (e.g., using a spatula or scoop), or by attachment to the surface of a device. When the tissue site is not exposed (e.g., at a wound site, a surgical site, or an otherwise accessible site such as a topical site), injection is a convenient route; if the site is exposed, such as an open wound, then any tool that can place granules in the site is satisfactory. In cases where granules are to be delivered at a site as protection for an implantable device, granules can be attached to surfaces of the device.

Granules may be injected dry as manufactured, or suspended in a biocompatible carrier fluid. In the case of certain biomaterials, such as cross-linked hyaluronic acid, additional further drying of the granules can extend shelf-life. Such granules can be dried by lyophilization, by air-drying (with or without heat), or chemically and can be rehydrated before use. Most often granules will be injected as a slurry. While any liquid that is biocompatible and that will flow through a needle is suitable, it may be desirable to use a biocompatible liquid that has lubricious properties. Other properties that may be desirable include bioresorption. Examples of suitable liquids include physiologic saline, buffered saline, sodium hyaluronate in water (e.g., at 0.1%, 0.25%, 0.5%, 0.75%, 1%, 1.25%, 1.5% concentrations), and buffered sodium hyaluronate in water. The carrier liquid may also contain a chemical or biological substance as described above. If desired for storage the liquid may also contain one or more preservatives, such as thimerosal, phenol, benzethonium chloride, or 2-phenoxyethanol. In slurry form, granules may be injected by a needle of inner lumen size that is approximately the smallest dimension of the granules. For example, granules that are sized to be 0.2 mm suspended in 1% sodium hyaluronate may be delivered via a 25 gauge needle (lumen diameter 0.2441 mm). Since the materials suitable to make granules are often soft and have open pores, individual granules can often be recoverably compressed and on occasion smaller needles may be used. Any tissue in the body is a candidate to receive granules. While soft tissues may often be sites for delivery of granules, harder tissues such as bone, are also candidates for injection of granules into cavities or fractures.

When a site is exposed, such as an open wound, abscess, fistula, or other externally accessible body area, granules may be applied with any suitable tool. For this type of application, a supply of granules may be inserted into the exposed cavity with a spatula, syringe, etc., and may be held in place by a dressing or by suturing the tissue over the site. In some circumstances, granules are first formed into clusters, held together by an adhesive, usually a biodegradable adhesive. Granules may also be attached temporarily or more permanently to a swatch of material, such as a wound pad or adhesive bandage used to cover an open wound, or to a guide wire or stick-like applicator that can be used to enter a fistula or other body cavity. Many such medical devices are commonly used in medical and veterinary practice and will be familiar to a person of ordinary skill in the field. In other circumstances, additives are co-delivered with the granules. Exemplary additives include drugs, antibiotics, growth factors and others disclosed herein, such as those discussed above.

Thus, one embodiment provides a biocompatible scaffold comprising one or more granules made of a porous biocompatible material having a plurality of substantially connected pores, wherein pores within the granules range from about 5 µm to about 100 µm in diameter and wherein each granule has a volume that is at least the volume of a sphere of at least about 0.1 mm and not more than the volume of a sphere of about 2 mm diameter equivalent, and wherein the granules are arranged such that they define interstitial spaces, a dimension of the interstitial spaces being about 15% to about 60% of a diameter equivalent of each granule.

Uses of Granules

Granules have many possible uses, some of which are discussed above. Some non-limiting examples of uses include filling a wound cavity, fistula or otherwise accessible damaged body area, reshaping a tissue, reconstructing damaged tissue areas, reducing a foreign body reaction (e.g., fibrosis) in vivo, delivering bioactive molecules, and providing sensor capabilities.

Figure 3:
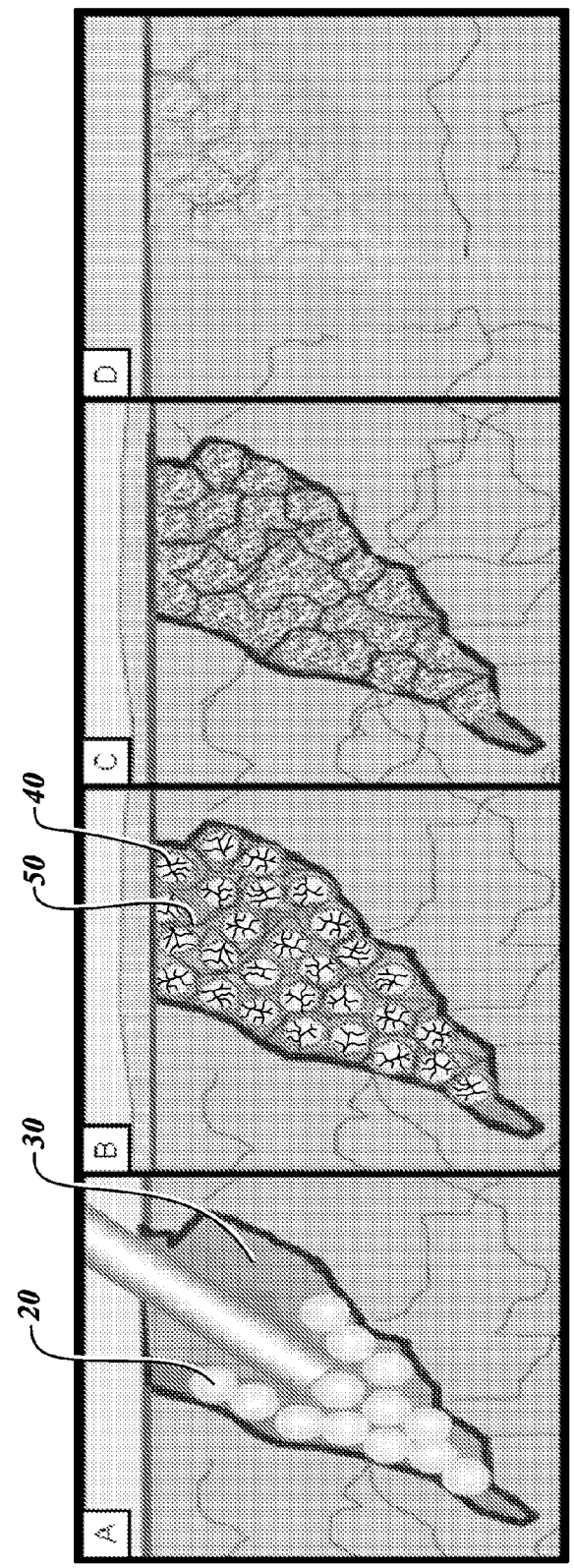
FIG. 3 is an illustration of granules injected into a wound cavity and the resulting healing response. Panel A depicts granules being injected into a wound cavity. Panel B depicts growth of capillaries in pores and growth of larger blood vessels in the interstitial spaces among granules. Panel C demonstrates fully vascularized granules. Panel D depicts replacement of degradable granules with healthy tissue.

As discussed above, granules may be used to improve or accelerate wound healing (FIG. 3). In the drawing, granules 20 are injected into the wound cavity 30 (panel A), although as discussed herein, there are many other ways to place granules in a cavity. Capillaries 40 are shown to grow in the pores and larger vessels 50 will grow in the interstitial spaces among and between granules (panel B). As vascularization increases, there is delivery of oxygen and nutrients to surrounding tissue (panel C), which in turn allows faster wound healing time and less scarring as the granules are infiltrated and surrounded, and then replaced, by healthy tissue (panel D). In the illustrated example the granules are made of a generally biodegradable substrate, such as cross linked hyaluronic acid. In other cases the granules may be of non degrading material such as silicone.

Externally accessible wounds often occur as a result of an accident or injury, but may also be caused by surgical techniques. Pressure ulcers (e.g., bed sores), diabetic ulcers, and other types of chronic wounds are especially difficult to heal and can require extensive treatments and management. In the science of wound bed preparation, problems in treating wounds, and especially chronic wounds, remain a serious medical concern, where increasing the healing rate is a paramount goal in wound therapy. Available advanced wound care methods presently use custom-shaped cavity filling pads, alone or in conjunction with negative pressure therapy, but may not be suitable for many situations where rapid wound healing is desired. Other types of cavity filling pads include foam-type pads that are not readily custom-shaped and so may not adequately or uniformly fill the void.

To address these and other limitations of previously available wound care methodologies, the presently described porous granules may conveniently be used to replace custom-shaped pads and/or the "one size fits all" type of pad. For filling open wounds, granules may be poured, injected, spooned or otherwise placed into the wound cavity. Because of their free-flowing nature, the herein-disclosed granules will "self-mold" to the precise shape of the cavity. When the cavity is sufficiently filled with granules, a dressing may be used to cover the wound and help keep the granules in place. The size of the granules for filling wounds is typically about 0.1 mm to about 2 mm diameter equivalent (diameter equivalent is the diameter of a sphere with the same volume as a granule) or any range between about 0.1 mm and about 2 mm. The maximum upper size of the granules will depend on part on the opening size of the granule applicator, in the case of a syringe or other similar type of applicator. If granules are poured into the wound cavity, there is no upper limit placed on the size of granules by the applicator.

The granules can be applied to an open wound as dry granules or as a slurry in a liquid. When applied dry, the granules absorb bodily fluids into the pores as a transport media for cell infiltration. When using a slurry, the liquid will generally be biocompatible and resorbable and usually have high viscosity and lubricious properties to aid in delivery. A typical liquid is 1% sodium hyaluronate. Other concentrations of sodium hyaluronate can also be used, or other degradable viscous fluids such as dilute fibrin or collagen solutions. A high viscosity delivery fluid ensures that the granules are pushed along the applicator lumen with the fluid, otherwise the fluid can flow around the granules or percolate through the pores. Higher concentration solutions will usually be more viscous and may influence the type of applicator that can be used, because higher viscosity may result in more pressure being used to force the liquid through a syringe, with or without a needle. Other suitable biocompatible liquids include normal saline, normal buffered saline or buffered water, including borate buffer, acetate buffer, and phosphate buffer. Furthermore, as discussed above, bioactive molecules may be added. In particular, growth factors that accelerate wound healing and antibiotics may be desirable additives, either incorporated into the granules or separately.

Wounded tissues may also occur as a result of internal injury, such as torn muscles or ligaments or torn capsules of organs; surgical intervention, such as removal of a tumor or normal tissue; placement or removal of an implanted device; disease, such as liver damage due to hepatitis, muscular wasting from diseases like muscular dystrophy, nerve damage due to any of a number of diseases and conditions (e.g., neurodegenerative diseases or neuropathies including neuropathies resulting as undesired drug side-effects), and the like. Granules may be used to fill the cavities. For these types of wounds, granules may be delivered by syringe, with or without a needle, or by another type of tool that can gain access to the wounded site. For delivery by syringe, granules will typically be suspended in a liquid, and usually the liquid will be lubricious. Additives such as growth factors may also be delivered with the granules, either incorporated into the granules or separately. The choice of additives or composition of granules will depend at least in part on the tissue at the site of delivery. For example, granules destined for damaged areas in bones may be comprised of or delivered with osteoinductive material, such as bone matrix proteins, growth factors like bone morphogenetic proteins, transforming growth factor, or osteoinductive-sensitive material, such as material sensitive to ultrasound (Habibovic and deGroot, *J Tissue Eng Regen Med:* 1:25, 2007). Cells such as mesenchymal stem cells, embryonic stem cells, and osteoblasts may also be delivered along with granules, as contemplated according to certain exemplary and non-limiting embodiments.

Granules may also be used to reshape tissues, by acting as a tissue expander. For instance, reconstructive surgery often entails reshaping tissues due to diseases, injuries and defects as well as for cosmetic purposes. Reconstructive surgeries include craniomaxillofacial reconstruction (e.g., wounded tissue restoration, repair of fractures, removal of tumors, cleft lip and palate repair, face-lifts, cheek augmentation, lip enhancements, wrinkle removal). Currently used cosmetic wrinkle removal or plumping injections have a limited time of effectiveness. As currently practiced, the material that is injected—e.g., collagen or hyaluronic acid gel—generally absorbs into the body over a 3-6 month period. The tissue relaxes and therefore reverts to its initial configuration, and repeated treatment is required to maintain a desired appearance. By contrast, according to herein disclosed embodiments using the present granules as a scaffold for reconstructive and plastic surgery, new tissue grows in the treated area and, by virtue of the advantageous promotion of angiogenesis and reduction of foreign body response (FBR) or undue inflammation, results in a permanent treatment. Granules can be used in any area where such tissue expansion is desired. Granules may be formed from bio-absorbable substrates or from permanent substrates, or a combination of both.

The following examples are offered by way of illustration, and not by way of limitation.

EXAMPLES

Example 1

Manufacture of Granules Formed of Poly(2-HYDROXY-ETHYL METHACRYLATE)

This example describes production of granules made of a porous biocompatible material.

Poly(methyl methacrylate) (PMMA) beads with diameter 36 micrometers +/−2 micrometers were added to polyether ether ketone (PEEK) molds consisting of a cavity about 3 cm long×2 cm wide×0.5 cm deep, and sintered for 19 hours at 190 degrees C. to give neck sizes of about 40% of the bead diameter. These fused-bead pore templates were infiltrated with a polymer precursor comprising the components in Table 1.

TABLE 1

| Polymer Precursor Mixture | |
| --- | --- |
| COMPONENT | VOLUME (ML) |
| 2-hydroxyethyl methacrylate (HEMA) | 7.0 |
| Ethylene glycol | 2.1 |
| Tetraethylene glycol dimethacrylate | 0.31 |
| Ammonium persulfate (0.4 g/mL) | 0.7 |
| Sodium metabisulfite (0.15 g/mL) | 0.7 |
| Endotoxin-free water | 1.4 |

The mixture was allowed to polymerize for 24 hours to provide polyHEMA impregnated with PMMA beads. The polymer was ground with a rotary blade coffee grinder. Granules were sieved, and the size fraction passing through 0.7 mm openings, but retained by 0.3 mm openings, was collected for use.

The PMMA pore templates were removed from the granules by Soxhlet extraction in dichloromethane.

The granules were transferred to acetone to swell the polyHEMA, then rinsed by Soxhlet extraction in endotoxin-free water for 2 hours with the condenser turned off (to boil off the acetone and dichloromethane) followed by 4 hours of Soxhlet rinsing with the condenser running.

Example 2

Tissue Ingrowth into Granules Implanted in Vivo

A 1 wt % sodium hyaluronate solution was prepared from endotoxin-free water and sodium hyaluronate powder, 2.59× $10^6$ Daltons MW (Lifecore Biomedical. Chaska Minn.). The solution was sterilized by exposing to ultraviolet light.

Granules of 0.3 -0.7 mm dimensions were prepared from poly(HEMA) per Example 1 and suspended in the sodium hyaluronate solution. The resultant slurry was loaded into 0.2 mL hypodermic syringes and injected subcutaneously into mice via 18-gauge needles.

The tissue response was evaluated at 7 and 28 days post-implantation.

Figure 4:
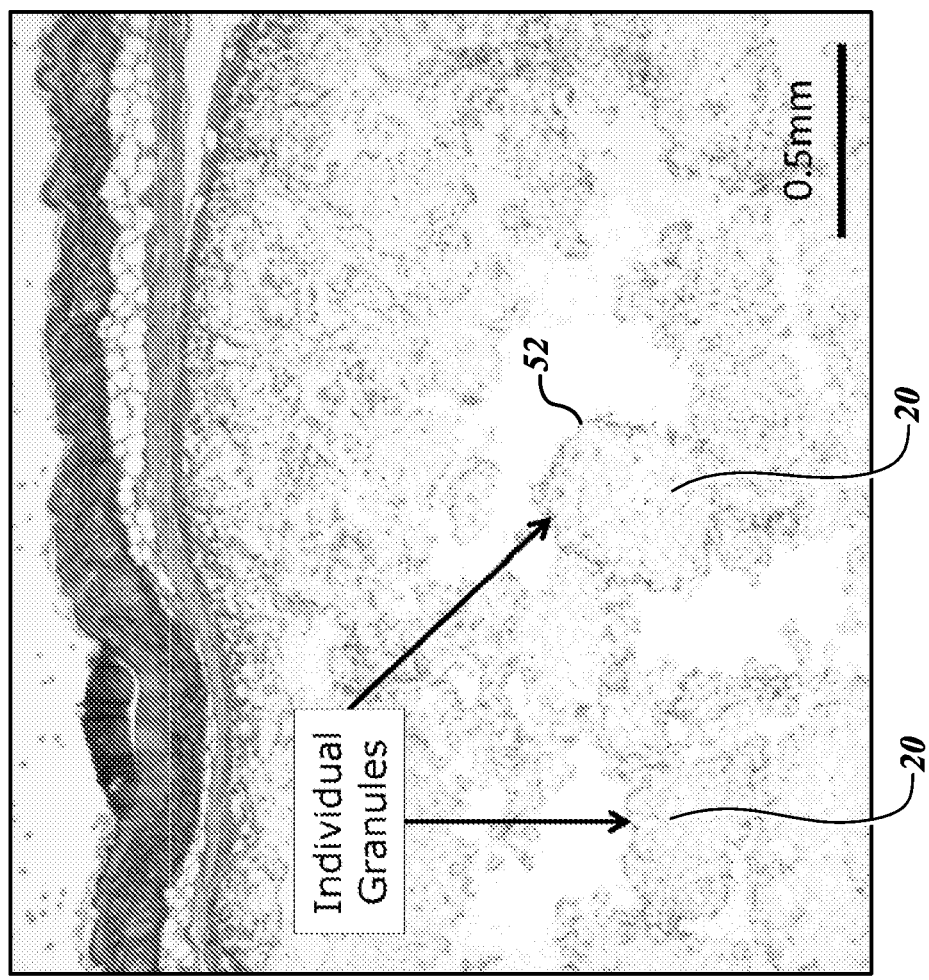
FIGS. 4 and 5 show histology from an in vivo experiment characterizing a physiological reaction to subcutaneously injected granules in mice.

FIG. 4 shows histology of the response at 7 days. The outlines 52 of the individual granules 20 were still clearly visible, apparently separated by carrier fluid. The periphery of each granule exhibited ingrowth and angiogenesis.

Figure 5:
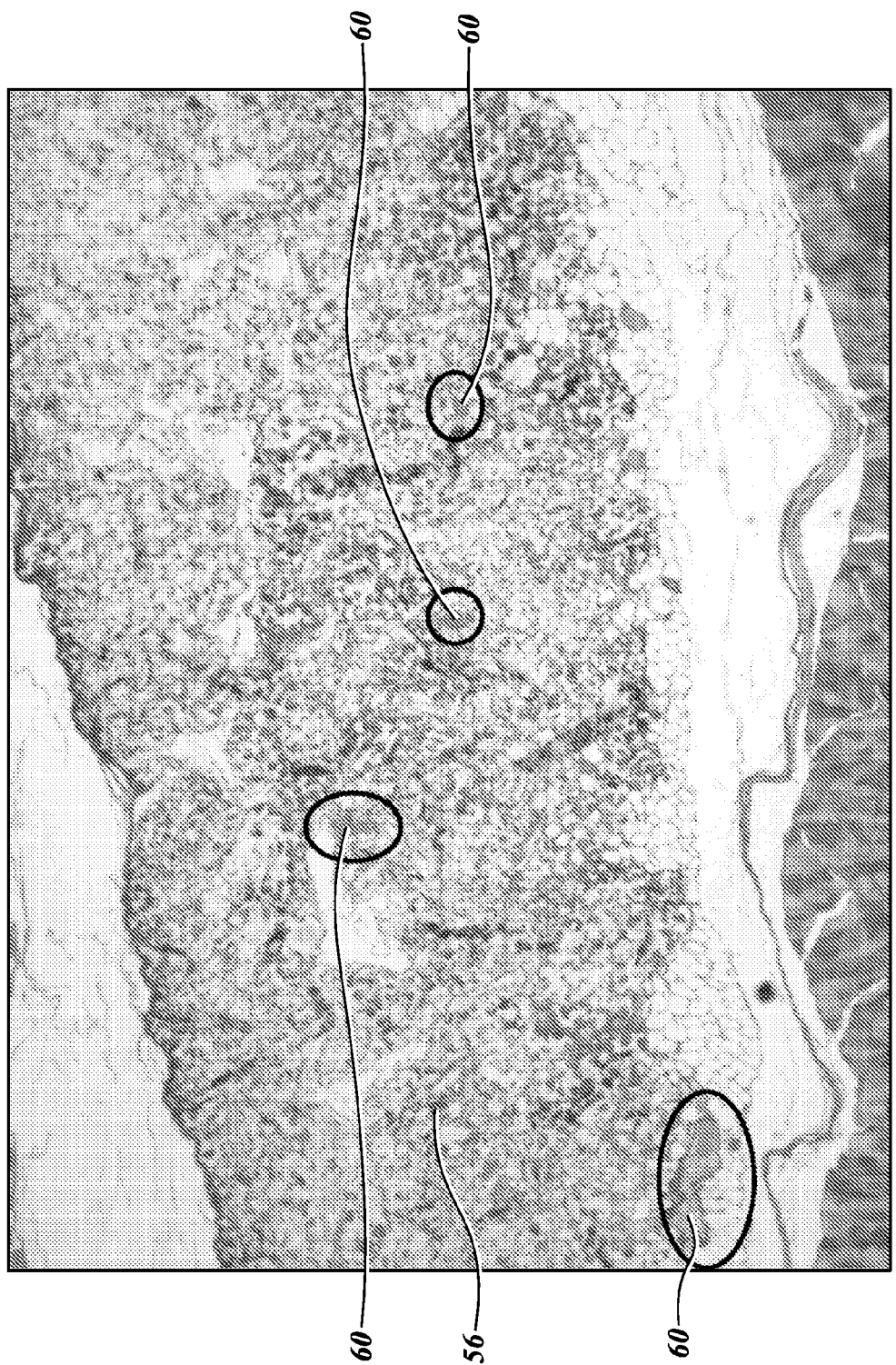

FIG. 5 shows results at 28 days. The carrier liquid is shown to have been absorbed into the surrounding tissue, leaving more completely packed granules. These granules exhibited complete tissue ingrowth 56 and between granules larger blood vessels 60 (circled) were detected.

Example 3

Manufacture of Granules Formed of Silicone

Monodisperse 27 μm thermoplastic acrylic beads were thoroughly sieved between meshes of 25 μm and 35 μm opening sizes using a RX-29 RoTap automatic sieve shaker (WS Tyler, Mento, Ohio) to remove undersized beads as well as any macro size particulate contaminants larger than the beads.

The beads were transferred to a rectangular mold (3 cm×2 cm×1 cm) and placed in a convection oven for 20 h at 180° C. to sinter the beads to approximately 11 μm interbead neck diameter.

The sintered bead "brick" was removed from the mold and impregnated with catalyzed NuSil MED-4211 silicone by centrifugation for 1 h at 30,000-g. After impregnation with silicone, the brick was placed in an oven at 80° C. for 16 h to cure the silicone.

Excess silicone was peeled from the outer surfaces of the brick to ensure that no granules would have surfaces skinned over with silicone.

A rotary blade coffee grinder was used to grind the brick into granules approximately 400 μm in diameter. The granules were then thoroughly sieved with a RoTap automatic sieve shaker to remove particles smaller than 300 μm or larger than 500 μm. Light microscopy was used to verify that >90% of granules of were within the target range.

Following sizing, the granules were stirred in dichloromethane for an initial extraction of the acrylic beads. Soxhlet extraction in dichloromethane was used to remove residual acrylic. Subsequent Soxhlet rinses in acetone followed by endotoxin-free water were used to boil off residual solvents. Scanning Electron Microscopy (SEM) was used to verify that mean throat size of the granules was between 10 and 12 μm.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A composition comprising a plurality of granules suspended in a biocompatible fluid the plurality of granules consisting of a porous synthetic polymer, the porous synthetic polymer having a plurality of substantially connected pores, wherein pores within the granules range from about 20 μm to about 90 μm in diameter and wherein each granule has a volume that is at least the volume of a sphere of at least about 0.1 mm diameter equivalent and not more than the volume of a sphere of about 2 mm diameter equivalent, wherein the granules are capable of being recoverably compressed, and wherein the porous synthetic polymer is selected from the group consisting of poly (2-hydroxyethyl methacrylate) (HEMA), medical-grade silicone, poly (epsilon-caprolactone) dimethylacrylate, polysulfone, (poly)methyl methacrylate (PMMA), soluble copolymers of tetrafluoroethylene and perfluoro-2,2-dimethyl-1,3-dioxole, polyethylene teraphthalate (PET), nylon, polyvinyl alcohol, polyurethane, and mixtures thereof.

2. The composition of claim 1, wherein the volume of an individual granule is not more than the volume of a sphere of about 1 mm diameter equivalent.

3. The composition of claim 1, wherein the volume of an individual granule is at least the volume of a sphere of about 0.1 mm diameter equivalent and not more than the volume of a sphere of about 0.4 mm diameter equivalent.

4. The composition of claim 1, wherein each granule has an internal porosity of about 60% to about 75%.

5. The composition of claim 1 wherein each granule has an aspect ratio of not more than 5.

6. The composition of claim 1 wherein the pores within each granule have a mean diameter of between about 20 μm and 40 μm.

7. The composition of claim 1 wherein two connecting pores within a granule define a throat diameter that is about 15% to 40% of the diameter of each of the two connecting pores.

8. The composition of claim 1, wherein the biocompatible fluid is bioresorbable.

9. The composition of claim 1, wherein the biocompatible fluid comprises sodium hyaluronate or saline.

10. The composition of claim 1, wherein the composition is injectable through a needle having a lumen smaller than the smallest diameter equivalent of the granules.

11. The composition of claim 1, wherein the biocompatible liquid is bioactive or comprises a bioactive ingredient.

12. The composition of claim 11, wherein the bioactive ingredient is an antibiotic, a drug, or a growth factor.

13. the composition of claim 1, wherein the porous synthetic polymer is medical grade silicone.

14. The composition of claim 1, wherein the porous synthetic polymer is poly (2-hydroxethyl methacrylate).

15. The composition of claim 1, wherein the composition further comprises a drug or a sensor of a body condition.

16. The composition of claim 1, wherein the composition is suitable for effecting tissue ingrowth when introduced into soft tissue.

* * * * *